(12) United States Patent
Bricker et al.

(10) Patent No.: US 7,267,987 B2
(45) Date of Patent: *Sep. 11, 2007

(54) PROCESS AND ASSEMBLY FOR SIMULTANEOUSLY EVALUATING A PLURALITY OF CATALYSTS

(75) Inventors: Maureen L. Bricker, Buffalo Grove, IL (US); J. W. Adriaan Sachtler, Des Plaines, IL (US); Charles P. McGonegal, Addison, IL (US); Mark A. Krawczyk, Chicago, IL (US); Ara J. Alexanian, Des Plaines, IL (US); Martin Plassen, Oslo (NO)

(73) Assignee: UOP LLC, Des Plaines, IL (US)

( * ) Notice: Subject to any disclaimer, the term of this patent is extended or adjusted under 35 U.S.C. 154(b) by 628 days.

This patent is subject to a terminal disclaimer.

(21) Appl. No.: 10/336,907

(22) Filed: Jan. 6, 2003

(65) Prior Publication Data
US 2004/0132194 A1 Jul. 8, 2004

(51) Int. Cl.
*G01N 31/10* (2006.01)
*B01J 8/00* (2006.01)
(52) U.S. Cl. ............... 436/37; 422/129; 422/130; 422/196; 436/43; 436/52; 436/155; 436/158; 436/159; 436/181
(58) Field of Classification Search ............ 422/62, 422/99–104, 129–131, 172, 196; 436/37, 436/43, 52, 155, 157–159, 181, 183
See application file for complete search history.

(56) References Cited

U.S. PATENT DOCUMENTS

| | | | | |
|---|---|---|---|---|
| 3,501,548 A | * | 3/1970 | Doane et al. | 585/623 |
| 3,753,653 A | * | 8/1973 | Brieva et al. | 436/139 |
| 4,469,146 A | * | 9/1984 | Campbell et al. | 141/9 |
| 4,737,262 A | * | 4/1988 | Franck et al. | 208/65 |
| 5,304,354 A | * | 4/1994 | Finley et al. | 422/196 |
| 5,435,171 A | * | 7/1995 | Chino et al. | 73/64.56 |
| 6,149,882 A | | 11/2000 | Guan et al. | 422/211 |
| 6,333,196 B1 | | 12/2001 | Willson, III | 436/37 |
| 6,342,185 B1 | | 1/2002 | Dahl et al. | 422/82.12 |
| 6,368,865 B1 | | 4/2002 | Dahl et al. | 436/37 |
| 6,395,552 B1 | | 5/2002 | Borade et al. | 436/37 |
| 6,410,332 B1 | | 6/2002 | Desrosiers et al. | 436/37 |

(Continued)

FOREIGN PATENT DOCUMENTS

JP 2002005918 A 1/2002

(Continued)

OTHER PUBLICATIONS

Hogan, R. J. et al, Preprints—American Chemical Society, Division of Petroleum Chemistry 1971, 16, D35-D42.*

(Continued)

*Primary Examiner*—Arlen Soderquist
(74) *Attorney, Agent, or Firm*—Maryann Maas

(57) ABSTRACT

A process and an assembly for simultaneously evaluating a plurality of catalysts is provided wherein the flow rate of a reactive fluid to each of a plurality of reactors is automatically adjusted based on the measured amount of catalyst sample in each reactor to concurrently obtain a substantially identical fluid space velocity in each of the reactors.

16 Claims, 1 Drawing Sheet

U.S. PATENT DOCUMENTS

| | | | |
|---|---|---|---|
| 6,489,168 | B1 | 12/2002 | Wang et al. .................. 436/37 |
| 6,548,305 | B1* | 4/2003 | Deves et al. .................. 436/37 |
| 6,551,832 | B1* | 4/2003 | Deves et al. .................. 436/37 |
| 2001/0034064 | A1 | 10/2001 | Turner et al. ................. 436/34 |
| 2001/0051376 | A1 | 12/2001 | Jonker ......................... 436/37 |
| 2001/0053528 | A1 | 12/2001 | Boussie et al. ............. 435/7.1 |
| 2002/0029623 | A1 | 3/2002 | Hajduk et al. ................. 73/81 |
| 2002/0045265 | A1 | 4/2002 | Bergh et al. .................. 436/37 |
| 2002/0090728 | A1 | 7/2002 | Shair et al. ................... 436/34 |
| 2003/0087442 | A1* | 5/2003 | Popa-Burke et al. .......... 436/43 |

FOREIGN PATENT DOCUMENTS

| | | |
|---|---|---|
| WO | WO9919724 | 10/1998 |

OTHER PUBLICATIONS

Johnston, H. D. et al, Preprints—American Chemical Society, Division of Petroleum Chemistry 1983, 28, 960-972.*

Creer, J. G et al, Applied Catalysis 1986, 22, 85-95.*

Korf, C. J. et al, CSIR Report CENG 1986, 584, 31 pages.*

Kapteijn, F. et al, Industrial & Engineering Chemistry Research 1993, 32, 445-452.*

Kafarov, V. V. et al, Chemie Ingenieur Technik 1994, 66, 351-354.*

Callega, G. et al, Fuel 1995, 74, 445-451.*

Baumhardt-Neto, R. et al, Polymer Bulletin 1998, 40, 103-109.*

Owens, G. D. et al, Analytical Chemistry 1982, 54, 2347-2351.*

Maxwell, S. L., III et al, Nuclear Material Management 1990, 19, 199-202.*

Poche, D. S. et al, Journal of Applied Polymer Science 1997, 64, 1613-1623.*

McCabe, R. W. et al, Industrial & Engineering Chemistry Product Research and Development 1983, 22, 212-217.*

Nakazaki, Y. et al, Industrial & Engineering Chemistry Research 1989, 28, 1285-1289.*

Moldovan, D. G. et al, Advances in Chemistry Series 1990, 227, 45-50.*

Alcantara, R. et al, Journal of Automatic Chemistry 1994, 16, 187-193.*

Lucas, M. et al, Chemie-Ingenieur-Technik 1995, 67, 773-777.*

Wiersma, A. et al, Journal of Catalysis 1998, 177, 29-39.*

Rodemerck, U. et al, Chemie-Ingenieur-Technik 1999, 71, 873-877.*

Cong, P. et al, Proceedings of the National Academy of Sciences of the United States of America 1999, 96, 11077-11080.*

* cited by examiner

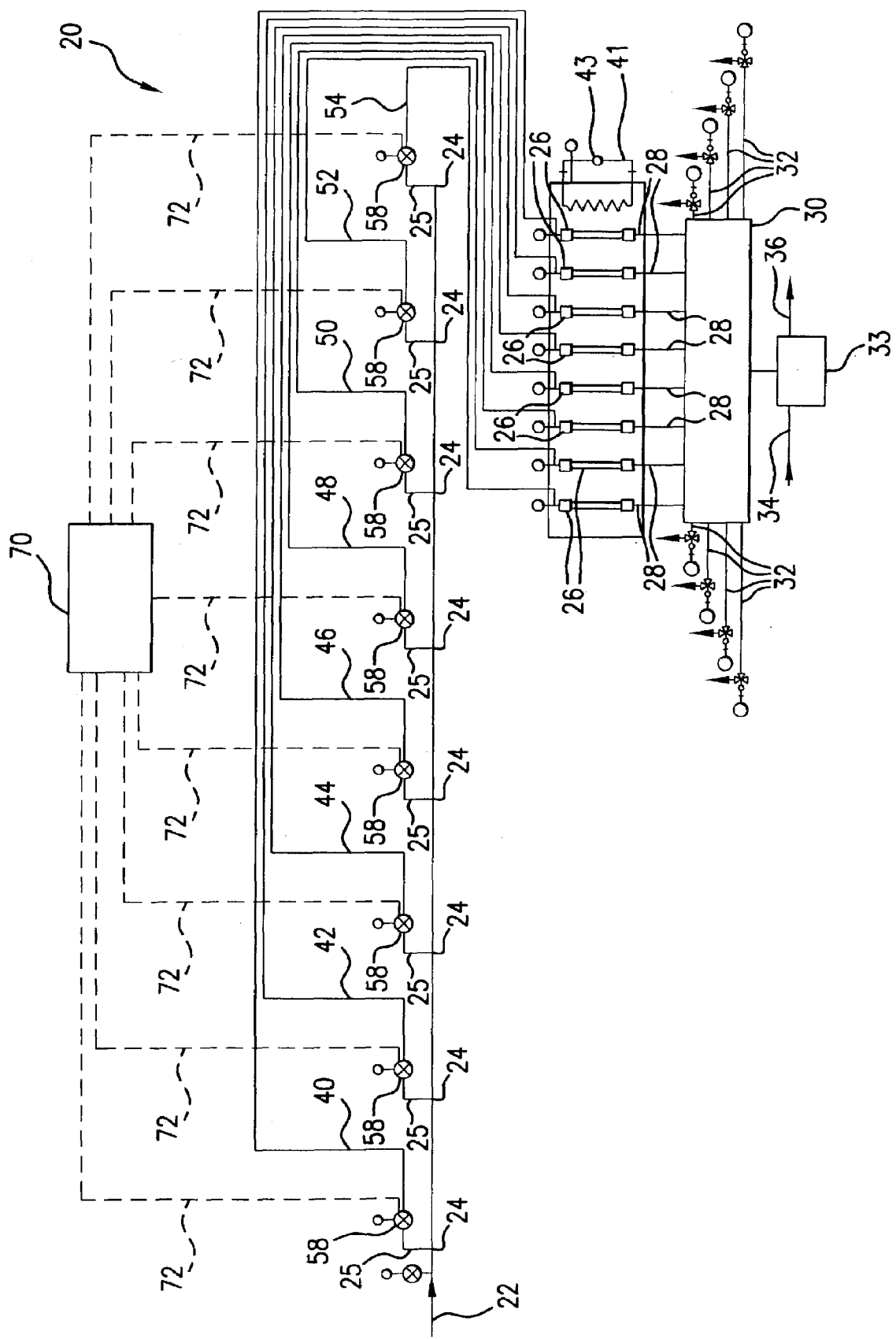

PROCESS AND ASSEMBLY FOR SIMULTANEOUSLY EVALUATING A PLURALITY OF CATALYSTS

FIELD OF THE INVENTION

This invention relates generally to the testing and evaluation of catalyst materials and, more particularly, to a process and assembly for simultaneously evaluating a plurality of catalysts.

BACKGROUND OF THE INVENTION

When formulating new catalysts, a large number of candidate catalyst compositions are typically synthesized. It then becomes important to evaluate the various candidate catalysts to determine and identify those formulations that are the most successful in catalyzing a particularly desired reaction under a selected set of reaction conditions. Activity and selectivity are two key characteristics of a catalyst that are commonly determinative of the success or desirability of the catalyst. The term "activity" commonly refers to the rate of conversion of reactants by a given amount of catalyst under specified conditions. The term "selectivity" commonly refers to the degree to which a given catalyst favors one reaction compared with other possible reactions. From the activity and selectivity values for a given catalyst, yields may be calculated. Thus, it is typically advantageous to evaluate or compare the performance of various catalyst materials based on the activity, selectivity and/or yield achieved with the various catalyst materials.

Traditionally, the activity, selectivity, and yield performance of a catalyst have been evaluated using a sequential approach. In such an approach, each catalyst sample or candidate is typically independently serially tested in a selected reactor at one or more sets of specified reaction conditions. In practice, suitable test reactors for particular applications may take various forms such as micro, pilot, bench-top and lab-scale reactors, for example. In most cases, such a test reactor is operated in a fixed bed mode. Alternatively, when the ultimate envisioned end use of a catalyst is in a fluidized bed application, catalyst samples may be tested using a test reactor operated in a fluidized bed mode. After completion of the tests at one or more sets of conditions, the tested catalyst sample is typically removed from the test reactor and the next catalyst sample is loaded into the respective reactor. The testing is then repeated on the freshly loaded catalyst sample. The process is repeated sequentially for each of the desired catalyst formulations. As will be appreciated, the application of such a process to the testing of numerous various catalyst formulations can be undesirably time-consuming.

Developments in combinatorial chemistry were at first largely concentrated on the synthesis of chemical compounds. Recently, combinatorial approaches have been applied to the testing of catalysts in an effort to expedite the catalyst evaluation process. The use of combinatorial approaches to catalyst evaluation has, however, been generally limited or restricted such as due to difficulties or an inability of ensuring the generation of a self-consistent combinatorial data set. In particular, combinatorial testing in which library members are evaluated at different space velocities typically results in data sets which are not self-consistent, e.g., performance differences may be at least in part attributable to differences in space velocities rather than to differences in the formulation of the various catalyst samples. For example, because a combinatorial approach commonly involves the loading of many samples for each run, the process of individually measuring out a specified weight for each sample can become extremely burdensome. Moreover, because combinatorial synthesis generally produces or results in a wide variety of materials such as may have widely varying properties, such as density, even reactors wherein materials have been loaded in a constant volume manner may contain significantly varying weights of material.

In view thereof, there is a need and a demand for procedural developments in combinatorial catalyst evaluation such as to better ensure self-consistent data sets such as by permitting or facilitating evaluation or comparison of each of multiple catalyst samples at a substantially identical space velocity. Further, there is a need and a demand for an assembly which facilitates and permits the generation of a self-consistent catalyst evaluation data set such as wherein each of multiple catalyst samples is concurrently evaluated at a substantially identical space velocity.

SUMMARY OF THE INVENTION

A general object of the invention is to provide an improved process and assembly for simultaneously evaluating a plurality of catalysts.

A more specific objective of the invention is to overcome one or more of the problems described above.

The general object of the invention can be attained, at least in part, through a process for evaluating a plurality of catalyst samples for catalysis of at least a portion of a fluid. In accordance with one preferred embodiment of the invention, such a process involves forming an array of a plurality of parallel reactors wherein each of the reactors contains a measured amount of at least one of the plurality of catalyst samples. A quantity of the fluid is passed to each of the reactors at a flow rate automatically adjusted based on the measured amount of the at least one of the plurality of catalyst samples in each reactor to concurrently obtain a substantially identical first space velocity in each of the reactors.

The invention further comprises an assembly for evaluating a plurality of catalyst samples for catalysis of at least a portion of a fluid wherein a measured amount of catalyst sample is disposed in each of an array of N parallel reactors. In accordance with one preferred embodiment of the invention, such an assembly includes at least N fluid flow regulators and a control unit in operational communication with the at least N fluid flow regulators. Each regulator is in fluid flow regulation communication with a corresponding one of the parallel reactors and is effective to regulate a rate of flow of the fluid to the corresponding one of the parallel reactors. The control unit is effective to automatically adjust the rate of flow of the fluid to the corresponding reactor based upon the measured amount of catalyst in the reactor, to concurrently obtain a substantially identical first space velocity in each of the reactors.

The prior art generally fails to provide processes and assemblies for the evaluation of a plurality of catalysts in a manner which is as effective as may be desired. In particular, the prior art generally fails to provide processes and assemblies conducive to a greater or more widespread use of combinatorial approaches to catalyst evaluation as prior combinatorial approaches to catalyst evaluation have typically been limited or restricted due to a difficulty or an inability of ensuring the generation of a self-consistent combinatorial data set.

As used herein and as identified above, references to catalyst "activity" generally refer to the rate of conversion of reactants by a given amount of catalyst under specified conditions and references to catalyst "selectivity" generally refer to the degree to which a given catalyst favors one reaction compared with another possible reaction.

References herein to space velocities as being "substantially identical" are to be understood to generally refer to space velocities that differ from one another by no more than about ±10% and, more preferably, differ from one another by no more than about ±6%.

"Weight Hourly Space Velocity", sometimes abbreviated as "WHSV", generally refers to the mass flow rate of total feedstock or selected feed component per mass of loaded catalyst, with units of inverse time, e.g., $hr^{-1}$.

"Liquid Hourly Space Velocity", sometimes abbreviated as "LHSV", generally refers to the volumetric flow rate of total feedstock or selected feed component (typically expressed at a reference temperature) per volume of loaded catalyst, with units of inverse time, e.g., $hr^{-1}$.

Other objects and advantages will be apparent to those skilled in the art from the following detailed description taken in conjunction with the appended claims and drawing.

BRIEF DESCRIPTION OF THE DRAWING

The FIGURE is a simplified schematic of an assembly for evaluating a plurality of catalyst samples in accordance with one preferred embodiment of the invention. The FIGURE illustrates only one of multiple banks of reactors.

DETAILED DESCRIPTION OF THE INVENTION

The present invention provides an improved process and assembly for simultaneously evaluating a plurality of catalysts.

In general terms, the present invention applies a combinatorial approach for simultaneously testing a plurality of catalyst samples. As described in greater detail below, the invention provides an approach that is rapid and yet provides an accurate basis for comparison of catalyst performance characteristics determined for each of a plurality of catalyst samples. The plurality of catalyst samples used in the practice of the invention may be any number beginning with at least two. Different catalyst samples may be of the same or a different formulation, or the same formulations may be present in different ratios of a mixture. Furthermore, identical catalyst sample formulations or mixtures may be repeated within the plurality, especially such as when statistical analysis are being conducted.

In accordance with the invention, an array of a plurality of parallel reactors is formed wherein each of the plurality of reactors contains a measured amount of at least one of the plurality of catalyst samples. The array of parallel reactors may be as few as two reactors, but preferably contains 6, 8, 12, 24, 48, 96, 384, or 1264 reactors. It is generally preferred that the array of parallel reactors be arranged in a row and column formation similar to that of a microtiter tray.

A common objective of catalyst evaluation testing is to produce or provide a comparison of yields, such as calculated from the activity and selectivity, based on the use of each of a plurality of catalyst samples in order to determine which catalyst sample is most suitable for use in connection with a given reaction. As identified above, to facilitate comparisons of yield, activity, and/or selectivity for various catalyst samples in a plurality, it is desirable that there exist a common basis for comparison. The present invention provides such a common basis for comparison for different catalyst samples by automatically adjusting the flow rate of fluid to each of the plurality of reactors based on the measured amount of the catalyst sample in each reactor to concurrently obtain a substantially identical fluid space velocity in each of the reactors.

Catalyst activity and/or selectivity may be determined from compositional analysis of each of the effluents (discussed in detail below), and the percent yield in each of the reactors of the array may be calculated. It is preferred to compare the percent yield of the catalyst samples to determine which of the catalyst samples exhibits the most preferred performance.

Those skilled in the art and guided by the teachings herein provided will appreciate that the broader practice of the invention is not necessarily limited by or to the mode of operation of the catalyst bed reactors employed in the practice of the invention. Thus, it will be understood that the invention can, if desired, be practice employing fixed or fluid bed reactors, as may be desired for specific applications. It is currently generally believed preferred that the invention be practiced employing or utilizing fixed bed reactors. In particular, fixed bed operation may generally be found easier to run as in typical fluidized bed operations the catalyst materials are generally only fluidized over a limited range of catalyst masses, particle sizes and flow rates whereas fixed bed operations generally do have such limitations. Furthermore, fixed bed operations can avoid difficulties that may be encountered with simulating fluidized bed hydrodynamic behavior on a micro-combinatorial scale as well as facilitate a system or assembly scale-up, such as may be desired for a commercial operation.

A fluid feed including one or more reactants is introduced to the catalyst bed reactor such as by any commonly known manner. The term "reactants" is sometimes used in the description of the process of the invention, but it should be understood that many chemical reactions require only a single reactant and the use of the plural form of the word reactant is for ease of explanation and not meant to limit the invention to only those reactions requiring more than one reactant. Thus, it is to be understood that the present invention can be successfully applied to chemical reactions having only one reactant as well as those having two or more reactants.

Those skilled in the art and guided by the teachings herein provided will also appreciate that the broader practice of the invention is not necessarily limited by or to application with particular or specific reactant feed materials. Further, particular fluid feeds used in the practice of the invention may additionally contain or include one or more diluents, co-reactants or additives such as known to those skilled in the art and guided by the teachings herein provided. For example, suitable diluents useable in the practice of the invention may include air, $N_2$, $H_2$, He, Ar; examples of suitable co-reactants useable in the practice of the invention may include air, $O_2$, $H_2O$, $H_2$, $N_2$, $Cl_2$ and $NH_3$ and examples of suitable additives useable in the practice of the invention include $H_2O$, $NH_3$, $H_2S$, CO, $CO_2$. It will be understood and appreciated by those skilled in the art and guided by the teaching herein provided that the particular classification of at least certain these materials can differ based on the specifics or particulars of the operation. Furthermore, the broader practice of the invention is not necessarily limited to or by the classification of a particular added feed material as a diluent, co-reactant or additive, for example.

Furthermore, those skilled in the art and guided by the teaching herein provided will appreciate that the invention can be suitably applied to the various reactions such as can be conducted in such reaction vessels such as, for example, including partial oxidations, CO and/or $NO_x$ removals, chlorinations and aminations as well as heterogeneous catalysis such as hydrocarbon conversions wherein a reactant feed is composed of one or more selected hydrocarbons and a co-reactant such as hydrogen, air or oxygen. Examples of hydrocarbons for which practice of the invention may have particular application include paraffins such as propane, butanes, pentanes, hexanes and heptanes; aromatics such as benzene, toluene, and xylenes; and naphthenes such as cyclopentanes and cylcohexanes. It is to be understood, however, that the broader practice of the invention is not necessarily limited to or by operation with particular hydrocarbons or the conversion thereof.

After introduction and contact with each of the respective catalyst samples, a reaction by or of the reactants may be catalyzed. Of course, since catalyst performance evaluation is a goal of the invention, it is expected that some of the catalyst samples tested will not catalyze the reaction at all, or perhaps only very little.

When the reactants contact the catalyst sample beds, an effluent is formed. In an embodiment wherein each reactor contains a catalyst sample composed of different catalysts or blend of catalysts, it is expected that the effluent may vary considerably from catalyst sample to catalyst sample. Consequently, some effluents may contain largely reactant or other fluid feed component, and other effluents may contain largely product, with a wide variety of feed to product ratios therebetween possible.

The effluents may in turn be analyzed using at least one selected analytical technique to determine whether products have been formed, how much product has been formed, and/or which specific product compounds have been formed. Those skilled in the art and guided by the teachings herein provided will appreciate that various analytical techniques may be used including any suitable technique for the type of information desired and components involved. In general, preferred techniques include, chromatography, spectroscopy, and nuclear magnetic resonance. Various different forms of chromatography and/or spectroscopy may be employed. Specific examples of chromatography and spectroscopy useable in the practice of the invention include liquid chromatography, gas chromatography, ultraviolet absorption spectroscopy, Raman spectroscopy, mass spectroscopy, visible absorption spectroscopy, ultraviolet-visible spectroscopy, atomic absorption spectroscopy, infrared absorption spectroscopy, and emission spectroscopy. While chromatography and spectroscopy methods are preferred, other acceptable techniques include but are not limited to fluorescence spectrometry, mass spectrometry, X-ray methods, radiochemical methods, electroanalytical methods, potentiometric methods, conductometric methods, electrogravimetric methods, coulometric methods, and voltammetry.

In accordance with one preferred embodiment of the invention, at least a portion of the effluent from each reactor is conveyed to the chosen analytical instrument. The effluents may be directly conducted to an analytical instrument, or aliquots of the effluents may be sampled and delivered to the location of the analytical instrument. In yet another embodiment, the effluents may be analyzed on-stream as they are removed from the reactors. In evaluating catalyst performance, observing trends of activity, selectivity, and yield over time can be valuable. Therefore, it may be desirable in particular applications that the effluent that is being withdrawn from each reactor be periodically or continuously analyzed as discussed above. Selectivity, activity, and/or yield may be determined upon the occurrence of each analysis, and trends in selectivity and/or activity observed over time. It is generally preferred that the effluents of each of the reactors be sampled simultaneously such that the analysis results are directly comparable and the time that each catalyst has been exposed to the reactant is the same. For quantitative results, the amounts of the effluents analyzed are measured. Alternatively, the reactors can be started sequentially to account for the offset in analysis time.

The specific analysis performed will typically depend on the particular application and desired information. For example, if only the activities of a plurality of catalyst samples are to be determined and compared, an effluent analysis measuring the amount of reactant consumed may be sufficient. Also, a qualitative analysis for the composition of the effluent can, if desired, be used as an indication of catalyst activity. However, it is generally preferred to have both activity and selectivity information and, in such instances, the analytical technique would be selected to measure the concentrations or quantities of the different components present in each effluent. Using information on both activity and selectivity, the yield of the desired products can be calculated and compared between the individual catalyst samples. It is preferred that the sampling of the effluent for each reaction be conducted simultaneously. A benefit of simultaneous sampling is that the results obtained for each catalyst bed are more readily comparable since each catalyst bed would have been exposed to the reactant for the same period of time. This is perhaps best understood via a description of an example. In a 48-reactor array with a single analyzer/detector, if the sampling of the 48 effluents were to occur sequentially, and the time needed for each sampling was one minute, there would be a 48 minute difference in time between sampling of the first and the last of the reactors. Therefore, the overall time the last catalyst sample would be exposed to the reactant would be 48 minutes longer than the overall time the first catalyst sample would be exposed to the reactant. It is known that the activity and selectivity of a catalyst may change over the period of time the catalyst is in use. Thus, during such a 48 minute time period between the sampling of the first and the last of the reactors, the activity and/or selectivity of the catalyst in the last reactor may have changed significantly as compared to that of the catalyst in the first of the reactors. Thus, it is to be appreciated that sequential sampling has an increased likelihood of introducing error since the period of time that a catalyst is in use, rather than being identical for all reactors, could become another variable to be accounted for in the analysis.

Turning to the FIGURE, there is illustrated a simplified schematic of an assembly, generally designated with the reference numeral 20, for evaluating a plurality of catalyst samples in accordance with one preferred embodiment of the invention. For ease of explanation, the process and apparatus will be described herein in reference to a 48-reactor system where the reactors are grouped into six banks, with each bank containing eight reactors. The FIGURE shows only the first bank of eight reactors. The other five banks of eight reactors each are not shown.

As shown, a reactant-including fluid feed stream feed stream 22 feeds into the assembly 20. The fluid feed is preferably gaseous but may be a liquid. The feed may be from cylinders and, if the feed is in the form of a gas, may be saturated with other components. In particular embodiments, the feed may be a liquid and such as processed through a pump (e.g., a syringe).

The reactant-containing fluid feed stream feed stream 22 is separated, via respective branch connectors 24, into eight separate portions, each designated by the reference numeral 25. The eight separated portions 25 are not regulated as to flow at this point. As described in greater detail below, the eight separated portions 25 are employed to form eight corresponding reactor feed streams individually designated 40, 42, 44, 46, 48, 50, 52 and 54, respectively.

The eight separated portions 25 are each simultaneously conducted through a respective flow regulator or controller 58 to form the eight corresponding reactor feed streams 40, 42, 44, 46, 48, 50, 52 and 54, respectively. Therefore, a set of eight flow controllers are used for each of the six banks of reactors. As will be appreciated, the invention advantageously allows or permits flow control to be conducted continuously over a range of fluid flow rates in a manner not allowed or permitted with systems which rely on the incorporation and use of fixed restrictors.

As described in greater detail below, the flow regulators 58 are used to individually regulate or control the flow rate of fluid feed in each of the reactor feed streams 40, 42, 44, 46, 48, 50, 52 and 54, respectively. Depending upon the application and the data desired or variables being investigated, the set of feed streams may be regulated or controlled to provide the same feed fluid flow to the reactors or they may be controlled at different flows. Those skilled in the art and guided by the teachings herein provided will appreciate that such flow regulation or control may be done on the basis of or in the form of gravimetric or volumetric flow regulation or control as may be desired for a particular application.

Each of the respective pressure transducers 60 monitors the pressure of the reactor feed in the respective feed line 40, 42, 44, 46, 48, 50, 52 and 54. The respective reactor feed streams are individually simultaneously introduced to a corresponding associated individual reactor 26. The reactors 26 may be of any type used in combinatorial evaluations, with preferred reactors being of the type described in EP 1108467 A2. As identified above, the number of reactors or vessels which make up the plurality may vary dependent upon the particular application and will typically vary between from two vessels to hundreds of reactors or vessels. Banks of reactors have generally been constructed in multiples of eight. Consequently, it is generally preferred to have at least eight reactors or vessels in the plurality.

The reactors 26 each houses or contains a measured amount of at least one of a plurality of catalyst samples. As identified above, each of the reactors may contain a catalyst sample composed of different catalyst materials, different mixtures of catalyst materials, or, alternatively, the same compositional mixture of catalyst materials but where the components are in different ratios, or the like. In addition, replicate catalyst samples may be included within the array of the parallel reactors.

The system assembly 20 also includes a control unit 70 in operational communication with the fluid flow regulators 58, as signified by the control lines 72, and effective to automatically adjust the rate of flow of the fluid to the respective corresponding reactors 26 based on the measured amount of catalyst in each reactor 26, to concurrently obtain a substantially identical space velocity in each of the reactors 26. As will be appreciated, various control units such as known to those skilled in the art and guided by the teachings herein provided are useable in the practice of the invention. Examples of such control units include Lab VIEW, available from National Instruments Corp., Honeywell DCS (distributed control system) and ABB Siemens DSC, for example.

Furthermore, in accordance with a preferred practice of the invention, such automatic adjustment of the rate of flow of the fluid to the reactors 26 can be preferably done continuously over a range of fluid flow rates such as to permit the obtaining of a substantially identical space velocity in each of the reactors without requiring that the reactors contain catalyst loads which are equal or differ from one another in any predetermined manner or by any discrete amount. As a result, the invention provides great flexibility in testing conditions while also simplifying and facilitating the manner of securing self-consistent data sets such as may be desired and useful in catalyst evaluations.

Those skilled in the art and guided by the teachings herein provided will appreciate that the fluid flow rate can be adjusted on a mass basis (e.g., mass flow rate) or a volumetric basis (e.g., volume flow rate), as may be desired in particular applications.

The effluent from each of the reactors 26 is conducted simultaneously, yet separately, in lines 28 to a sampling system 30 in order to sample the effluents for further processing such as analysis. The sampling of the effluent from each of the reactors 26 may be advantageously conducted simultaneously, as identified above. Alternatively, such sampling can be conducted in a sequential manner, if preferred.

When the effluents are not actively being sampled, the respective effluent can be conducted through an independent path, shown as the lines 32, to a proper venting system. As will be appreciated, dependent on the compounds employed and being treated in the system assembly 20, waste effluents may be treated to remove, convert or neutralize specific compounds, components or materials before being vented to the atmosphere. For certain applications, the effluents may be condensed and collected, such as for further use or disposal, as may be desired or appropriate therefor.

Joined to or connected with the sampling system 30 is a processing or analytical device, designated by the reference numeral 33. A gas chromatograph is an example of one suitable common form or type of analytical device for use in particular applications of the invention. As will be appreciated, however, other suitable types or forms of analytical techniques such as described above may be used or employed in the practice of the invention. Consequently, it is to be understood that the broader practice of the invention is not necessarily limited by or to operation with a specific or particular analytical technique or sampling procedure.

The analytical device 33 has an input or carrier stream 34 and an analytical device effluent stream 36.

In addition, the reactors 26 may be, if desired and as shown, associated with a heater 41 having a controller 43 to provide controlled heat to the reactors. Alternatively, individual heaters may be employed for each or selected of the reactors 26.

It will further be appreciated by those skilled in the art and guided by the teachings herein provided that the above described assembly 20 may additionally contain or include additional components or features such as pressure transducers, check valves and pressure controllers, for example, as may be desired in particular applications.

As identified above, each of the plurality of reactors contains a measured amount of a catalyst sample. Those skilled in the art and guided by the teachings herein provided will appreciate that various techniques or means are available and may be used to provide or ensure that a measured amount of catalyst sample is present in particular reactors of the plurality. For example, such measured amount of catalyst sample can be of determined on a gravimetric or volumetric basis. In accordance with one preferred embodiment of the invention, such gravimetric measurement may be via indirect weighing of the catalyst sample such as by weighing a holder portion of the reactor of interest, loading the catalyst sample into the weighed holder portion, followed by weighing the catalyst sample-loaded holder portion of the reactor of interest. As will be appreciated, such loading of catalyst samples may be done on a volumetric basis, such as in accordance with a preferred embodiment of the invention, via the loading of catalyst samples of substantially identical volume into the various of the plurality of reactors. In such indirect weighing of the catalyst sample, the amount of the catalyst sample generally corresponds to the difference between the weight of the catalyst sample-loaded holder portion and the weight of the empty holder portion. In accordance with another preferred embodiment of the invention, such gravimetric measurement may be via direct weighing of the catalyst sample.

In accordance with a preferred practice of the invention, the generation of a self-consistent catalyst evaluation data set is provided via concurrently evaluating each of the multiple catalyst samples at a substantially identical space velocity based on at least one of the fluid feed components. As will be appreciated by those skilled in the art and guided by the teachings herein provided, such space velocities may be determined on an appropriate selected basis such as a weight hourly space velocity or a liquid hourly space velocity, for example. Moreover, it is to be understood that while the broader practice of the invention is not necessarily limited to application with specific or particular space velocities, the invention is currently conceived as being particularly advantageous in applications wherein the substantially identical space velocity in each reactor of the array is in a range from about 0.1 to about 1000 $hr^{-1}$, with further specific embodiments having particular utility in applications wherein the substantially identical space velocity in each reactor of the array is in a range from about 300 to about 600 $hr^{-1}$ or, alternatively, in a range from about 1 to about 35 $hr^{-1}$. As will be appreciated, interest in particular or specific range or ranges of space velocities will generally be dictated by catalyst chemistry and kinetics with particular emphasis on catalyst chemistry and kinetics that permit commercially amenable space velocities.

If desired and as may be preferred, one or more or, if desired, all of the catalyst-loaded reactors of the array may, after a period of time, be tested at a second selected substantially identical space velocity such as where the second substantially identical space velocity is the same or different from the first substantially identical space velocity at which such catalyst-loaded reactors of the array were originally or previously tested. Furthermore, one or more or, if desired, all of the catalyst-loaded reactors of such an array may, after a period of time, be tested at a third selected substantially identical space velocity such as where the third substantially identical space velocity is the same or different from either or both the first and the second substantially identical space velocity at which such catalyst-loaded reactors of the array were originally or previously tested.

Thus, the invention provides a process and an assembly for simultaneously evaluating a plurality of catalysts at a substantially identical space velocity such as to better permit the evaluation of such catalysts on the basis of self-consistent data sets.

It will be appreciated by those skilled in the art and guided by the teachings herein provided that while the invention has been described above making specific reference to an embodiment wherein a constant data set is obtained via operation at substantially identical space velocities, the invention can, if desired, be practiced such that flows are appropriately adjusted to obtain or result in substantially identical conversions. Furthermore, a hybrid manner of testing or operation such employing both constant space velocity and constant flow rate steps can, if desired, be employed.

Moreover, the method of the invention can, if desired, be repeated for a previously tested catalyst sample at a space velocity that is the same or differs from that at which the catalyst sample was previously tested.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A process for evaluating a plurality of catalyst samples for catalysis of at least a portion of a fluid, the process comprising:
   forming a plurality of parallel reactors wherein each of the plurality of reactors contains a measured amount of at least one of the plurality of catalyst samples and wherein a quantity of the fluid flows to each of the plurality of reactors at an adjustable rate and wherein determining the measured amount of catalyst sample comprises the steps:
   weighing a holder portion of each reactor in the plurality of reactors;
   volumetrically loading catalyst samples into the weighed holder portions of the reactors;
   reweighing the catalyst sample-loaded holder portions of the reactors
   automatically adjusting the flow rate of the fluid to each of the reactors in the plurality of reactors independently based on the measured amount of catalyst samples in each reactor to concurrently obtain a substantially identical first space velocity in each of the reactors.

2. The process of claim 1 wherein the catalyst sample loaded into each of the plurality of reactors is substantially identical in volume.

3. The process of claim 1 wherein the flow rate of the fluid automatically adjusted is a mass flow rate.

4. The process of claim 1 wherein the flow rate of the fluid automatically adjusted is the volume flow rate of the fluid.

5. The process of claim 1 wherein the fluid comprises at least two components and the substantially identical space velocity in each reactor of the array is based on at least one of the fluid components.

6. The process of claim 1 wherein the substantially identical space velocity in each reactor of the array is a weight hourly space velocity or a liquid hourly space velocity.

7. The process of claim 1 wherein the substantially identical space velocity in each reactor of the array is in a range from about 0.1 to about 1000 $hr^{-1}$.

8. The process of claim 7 wherein the substantially identical space velocity in each reactor of the array is in a range from about 300 to about 600 $hr^{-1}$.

9. The process of claim 7 wherein the substantially identical space velocity in each reactor of the array is in a range from about 1 to about 35 $hr^{-1}$.

10. The process of claim 1 wherein each of the reactors has a corresponding fluid flow rate regulator in fluid flow regulation communication therewith and wherein the automatic adjustment of the flow rate of the fluid to each of the reactors comprises adjusting the respective regulator.

11. The process of claim 1 wherein the fluid comprises a reactant component and at least one of a co-reactant component and an inert component.

12. The process of claim 11 wherein the reactant component comprises a hydrocarbon material.

13. The process of claim 12 wherein the fluid comprises at least one of hydrogen, oxygen, air and $H_2O$.

14. The process of claim 1 additionally comprising automatically adjusting, after a period of time, the flow rate of the fluid to each of the reactors based upon the measured amount of catalyst in each reactor to concurrently obtain a substantially identical second space velocity in each reactor.

15. The process of claim 14 further additionally comprising repeating the step of automatically adjusting, after a period of time, the flow rate of the fluid to each of the reactors based upon the measured amount of catalyst in each reactor to concurrently obtain a substantially identical third space velocity in each reactor.

16. The process of claim 1 wherein the automatic adjustment of the flow rate of the fluid to each of the reactors is continuous over a range of fluid flow rates.

* * * * *

UNITED STATES PATENT AND TRADEMARK OFFICE
CERTIFICATE OF CORRECTION

PATENT NO. : 7,267,987 B2
APPLICATION NO. : 10/336907
DATED : September 11, 2007
INVENTOR(S) : Maureen L. Bricker et al.

Page 1 of 1

It is certified that error appears in the above-identified patent and that said Letters Patent is hereby corrected as shown below:

On the Title Page in the (*) Notice Section, the sentence "This patent is subject to a terminal disclaimer." should be deleted.

Signed and Sealed this
Eleventh Day of June, 2013

Teresa Stanek Rea
*Acting Director of the United States Patent and Trademark Office*